United States Patent
Wilhelm

(10) Patent No.: US 8,470,431 B2
(45) Date of Patent: Jun. 25, 2013

(54) PRODUCT WITH EMBOSSMENTS HAVING A DECREASING LINE WEIGHT

(75) Inventor: Lee D. Wilhelm, Appleton, WI (US)

(73) Assignee: Kimberly Clark

(*) Notice: Subject to any disclaimer, the term of this patent is extended or adjusted under 35 U.S.C. 154(b) by 699 days.

(21) Appl. No.: 11/957,055

(22) Filed: Dec. 14, 2007

(65) Prior Publication Data
US 2009/0155529 A1 Jun. 18, 2009

(51) Int. Cl.
*B32B 3/00* (2006.01)
*B31F 1/07* (2006.01)

(52) U.S. Cl.
USPC ........... 428/156; 428/172; 428/174; 428/212; 162/109; 162/113; 156/209

(58) Field of Classification Search
USPC ............. 428/156, 172, 174, 212; 162/109, 162/113; 156/209
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,494,821 A | 2/1970 | Evans | |
| 3,502,538 A | 3/1970 | Peterson | |
| 3,502,763 A | 3/1970 | Hartmann | |
| 3,531,920 A * | 10/1970 | Hart | 55/497 |
| 3,542,615 A | 11/1970 | Dobo et al. | |
| 3,692,618 A | 9/1972 | Dorschner et al. | |
| 3,718,531 A * | 2/1973 | Lewis | 428/172 |
| 3,802,817 A | 4/1974 | Matsuki et al. | |
| 3,849,241 A | 11/1974 | Butin et al. | |
| 4,100,324 A | 7/1978 | Anderson et al. | |
| 4,144,370 A | 3/1979 | Boulton | |
| 4,340,563 A | 7/1982 | Appel et al. | |
| 5,129,988 A | 7/1992 | Farrington, Jr. | |
| 5,284,703 A | 2/1994 | Everhart et al. | |
| 5,350,624 A | 9/1994 | Georger et al. | |
| 5,382,400 A | 1/1995 | Pike et al. | |
| 5,490,902 A * | 2/1996 | Schulz | 162/109 |
| 5,494,554 A | 2/1996 | Edwards et al. | |

(Continued)

FOREIGN PATENT DOCUMENTS

DE 202004011289 11/2004
EP 1331308 7/2003

(Continued)

OTHER PUBLICATIONS

International Paper—Embossing <http://web.archive.org/web/20051224121858/http://glossary.ippaper.com/default.asp?req=knowledge/article/209>; published Dec. 24, 2005.*

(Continued)

*Primary Examiner* — Donald J Loney
(74) *Attorney, Agent, or Firm* — Dority & Manning, P.A.

(57) ABSTRACT

Embossed sheet materials are disclosed. In accordance with the present disclosure, the embossing pattern includes at least one line element that has a gradually decreasing depth. The gradually decreasing depth has been found to alter the shadow characteristics of the embossing pattern thus creating a line in the embossing pattern that appears to decrease in line weight. The decrease in line weight is accomplished without having to change the width of the embossment, although the width can also be changed in conjunction with the depth. Being able to incorporate line weight variations into embossing patterns can dramatically improve the aesthetic appeal of the patterns.

19 Claims, 7 Drawing Sheets

U.S. PATENT DOCUMENTS

| | | | |
|---|---|---|---|
| 5,529,665 A | 6/1996 | Kaun | |
| 5,779,965 A | 7/1998 | Beuther et al. | |
| 5,792,545 A * | 8/1998 | Kawai et al. | 428/153 |
| 6,315,864 B2 | 11/2001 | Anderson et al. | |
| 6,348,131 B1 * | 2/2002 | Kershaw et al. | 162/112 |
| 6,440,564 B1 | 8/2002 | McClain et al. | |
| 6,506,324 B1 * | 1/2003 | Gerber | 264/40.1 |
| 6,680,102 B2 | 1/2004 | Graff | |
| 6,712,397 B1 * | 3/2004 | Mayer et al. | 283/91 |
| 6,896,767 B2 * | 5/2005 | Wilhelm | 162/117 |
| 6,918,993 B2 | 7/2005 | Tirimacco | |
| 7,252,870 B2 | 8/2007 | Anderson et al. | |
| 2003/0159600 A1 | 8/2003 | Ruthven et al. | |
| 2005/0035492 A1 | 2/2005 | Weiher et al. | |

FOREIGN PATENT DOCUMENTS

| | | |
|---|---|---|
| WO | 9631652 | 10/1996 |
| WO | WO 9934057 A1 | 7/1999 |
| WO | WO 0066835 A1 | 11/2000 |

OTHER PUBLICATIONS

English Abstract of JP 2008-323948, Published Dec. 10, 1996.
English Abstract of JP 2005-323904, Published Nov. 24, 2005.
PCT/IB2008/053890 International Search Report, Published Apr. 16, 2009.
Supplementary European Search Report, dated Aug. 17, 2012.

* cited by examiner

PRODUCT WITH EMBOSSMENTS HAVING A DECREASING LINE WEIGHT

BACKGROUND

During the production of many nonwoven materials, the materials are subjected to an embossing process. Embossing is a process of creating a 3-dimensional image or design into the sheet material. In one embodiment, a sheet material can be embossed by feeding the sheet material into a nip formed between an embossing roller and a backing roller. The embossing roller, for instance, may define a plurality of raised elements that form embossments into the sheet material. The embossments can be formed into the sheet material using pressure alone or in combination with heat.

Nonwoven materials that are typically subjected to embossing processes include various different tissue products, such as paper towels, napkins, bath tissue, facial tissue, premoistened wipes, and other products. The nonwoven materials can be embossed for many different reasons. For instance, embossing can be used in order to increase the bulk of the product, to improve the liquid absorption properties of the product, to increase the softness of the product or simply to improve the aesthetics of the product. Embossing can also be used to attach two or more plies of the nonwoven material together.

Regardless of the particular application, most embossing patterns are intended to improve the visual appeal of the product to consumers. Embossing patterns incorporated into tissue products and other similar materials, however, are not always completely visually perceivable. Much detail incorporated into such embossing patterns remains unnoticed.

For instance, graduated line weights are commonly used in decorative and geometric patterns to indicate flexibility, motion, perspective, and the like. Varying line weight generally means varying the thickness of a line in order to emphasize or de-emphasize different parts of the image. Varying the line weight in an embossed pattern by increasing or decreasing the thickness of the embossment, however, is not easily perceivable and thus has little effect on the overall aesthetic appeal of the pattern or design.

In view of the above, a need currently exists for a technique or method for creating a perceived line weight variation in an embossing pattern applied to a sheet material, such as a tissue product. Creating perceived line weight variations in patterns embossed into a nonwoven material can enhance the consumer appeal of the embossed product.

SUMMARY

In general, the present disclosure is directed to various embossed products and to a process for embossing sheet-like materials. In accordance with the present disclosure, heavier or shallower line weights are incorporated into the pattern embossed into a sheet-like product by increasing or decreasing the depth of the engraving. More particularly, the present inventor has discovered that perceived graduated line weights can be incorporated into an embossing pattern by gradually increasing or decreasing the depth of the embossments along a continuous line. In this manner, decorative patterns can be embossed into various sheet-like materials, including tissue webs, that have dramatically enhanced visual appeal.

In one embodiment, for instance, the present disclosure is directed to an embossed product comprising a base sheet containing natural fibers, synthetic fibers, or mixtures thereof. The base sheet includes a first side and a second and opposite side. A pattern is embossed into the first side of the base sheet. The embossed pattern includes at least one line element wherein the depth of the embossed pattern along the line element gradually decreases making the line element appear to have a decreasing line weight. The depth of the embossed pattern along the line element can gradually decrease in a stepwise manner or in a continuous manner.

In one embodiment, the line element can have a length of at least 0.5 inches. The depth of the embossed pattern along the line element can have a minimum depth and a maximum depth. The minimum depth can be from about 0.005 inches to about 0.1 inches. The maximum depth, on the other hand, can be from about 0.005 inches to about 0.06 inches greater than the minimum depth. For instance, in one embodiment, especially when embossing tissue products, the minimum depth and the maximum depth can fall within the range of from about 0.02 inches to about 0.15 inches. In one particular embodiment, the minimum depth can be about 0.02 inches and the maximum depth can be about 0.04 inches.

In one embodiment, the line element can also include a gradually changing width in addition to depth. For instance, in one embodiment, the width of the line element can also decrease as the depth of the line element gradually decreases.

As described above, changing the depth of the line element within the base sheet visually changes the line weight of the line element. In one embodiment, the line weight of the line element can appear to increase and decrease at desired locations. For instance, in one embodiment, the depth of the line element can gradually decrease and then gradually increase making it appear that the line element tapers and then expands along the plane of the base sheet.

In general, any suitable base sheet can be embossed according to the present disclosure. For instance, in one embodiment, the base sheet may comprise a tissue product containing pulp fibers in an amount of at least 30% by weight and having a bulk of greater than about 3 cc/g. The base sheet, for instance, may comprise a paper towel, a napkin, a facial tissue, a bath tissue, a premoistened wipe, and the like.

In an alternative embodiment, the base sheet may be made exclusively from synthetic fibers. For instance, the base sheet may comprise a meltblown web, a spunbond web, or another type of nonwoven material.

The base sheet can also be made from a single ply of material or can be made from a plurality of plies. In fact, in one embodiment, the embossing pattern may be used to attach two or more plies together.

The embossing pattern formed into the base sheet can also vary dramatically depending upon the particular application. The embossing pattern may comprise any suitable aesthetic design elements or geometric patterns. For instance, in one embodiment, the line element may be part of a decorative feature, such as a leaf, a plant, a flower, a caricature, or any other suitable design.

In order to produce embossed products in accordance with the present disclosure, in one embodiment, the base sheet can be fed into a nip formed between an embossing roller and a backing roller. The embossing roller can include raised portions that emboss a pattern into the base sheet. The raised portions can include at least one line portion that has a gradually decreasing profile for embossing a corresponding line element into the base sheet.

The embossing roller, for instance, can include a cylindrical surface from which the raised portions extend. The cylindrical surface can have a constant diameter or a changing diameter. When the cylindrical surface has a changing diameter, for instance, the embossing roller may be configured such that the top surface of each raised portion is equal distance to an axis defined by the embossing roller.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
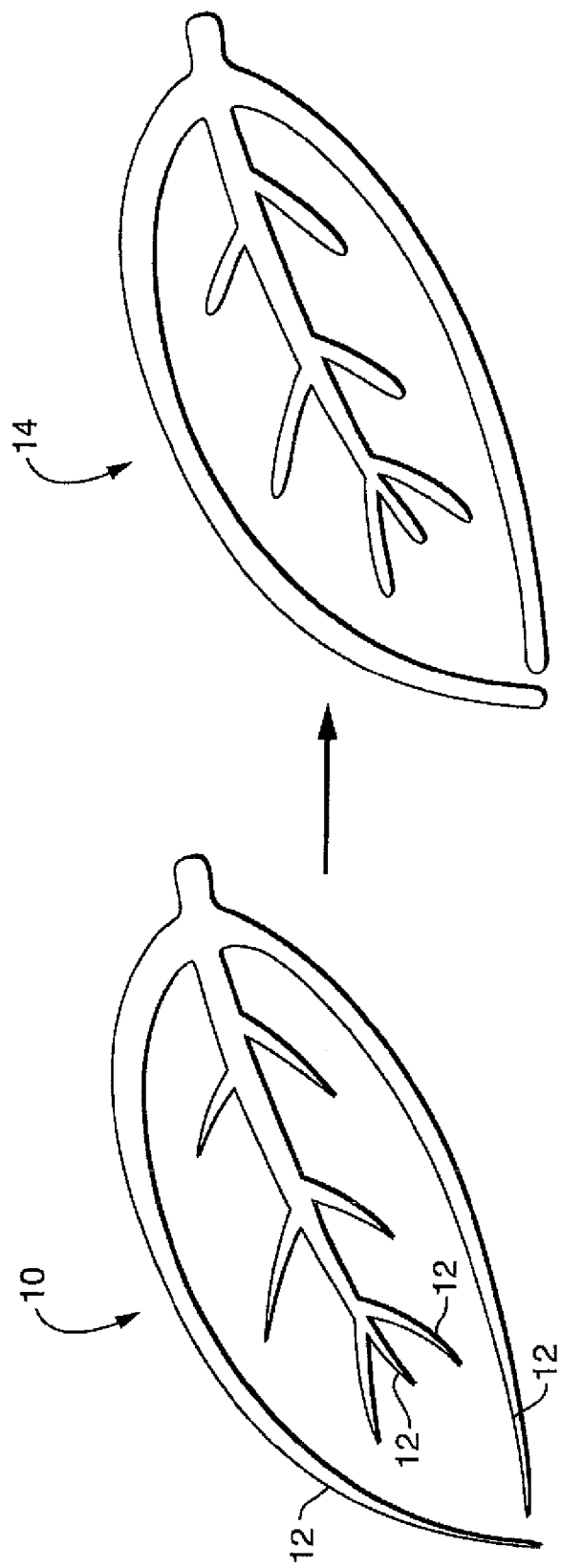
FIG. 1 is a diagram illustrating one of the problems solved by the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

Graduated line weights are commonly used in artistic renderings to indicate flexibility, motion, perspective and the like. In the past, however, problems have been encountered in visually showing graduated line weights in embossed sheet products, such as tissue products. For instance, referring to FIG. 1, an embossing element generally 10 is shown. The embossing element 10, in this embodiment, represents a leaf. As shown, the embossing element 10 includes areas 12 where the design includes graduated line weights to make the leaf more decorative.

When the embossing element 10 is embossed into a sheet of material, however, the graduated line weights are lost. For instance, the resulting embossment 14 is shown in FIG. 1 that is produced from the embossing element 10. More particularly, the embossment 14 is what is actually seen by the human eye when the embossing element 10 is used to emboss the sheet of material. As shown, the variations in line weight are no longer visible in the finished product.

The present inventor has discovered that line weight variations do not show up well in embossed sheet materials because the variation in the width of the design does not impact a shadow line generated by the 3-dimensional topography of the embossed line. For instance, designs and patterns embossed into sheet materials are best viewed under light with a low angle of incidence, where the light casts a shadow in the depressed area of the embossing. When the depressed areas of the embossing pattern, however, are at a constant depth, the width of the shadow remains constant regardless of the width of the depression.

In order to address the above problems and to create embossing patterns that have line weight variations, the present disclosure is directed to embossing patterns containing one or more line elements that have a gradually decreasing depth which alters the shadow characteristics of the pattern making line weight variations visible. Heavier or shallower line weights, for instance, can be shown in embossed sheet materials by increasing or decreasing the depth of the embossment respectively. Increasing or decreasing the height of the vertical wall in the embossed pattern has been found to correspondingly alter the width of the shadow cast by the embossment. Graduated line weights can thus be obtained by graduating the depth of the embossing pattern along a line. Further, embossed lines produced in the above fashion may have any desired variation in line weight from a simple graduation to a complex curve with multiple changes in weight as will be described in greater detail below.

Figure 8A:
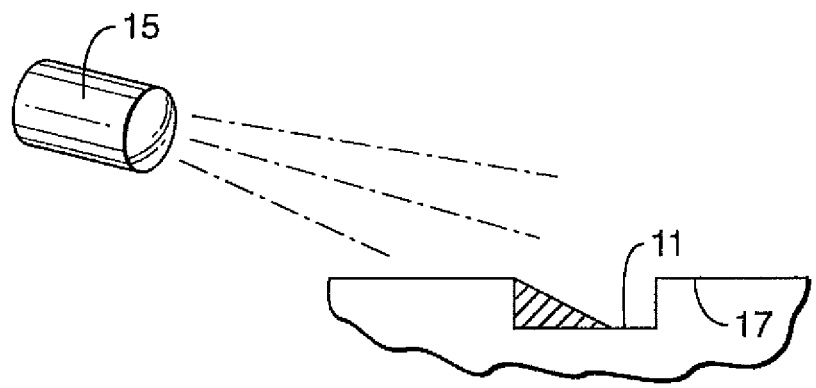
FIGS. 8A and 8B are demonstrative illustrations provided to assist in explaining the teachings of the present invention.
Figure 8B:
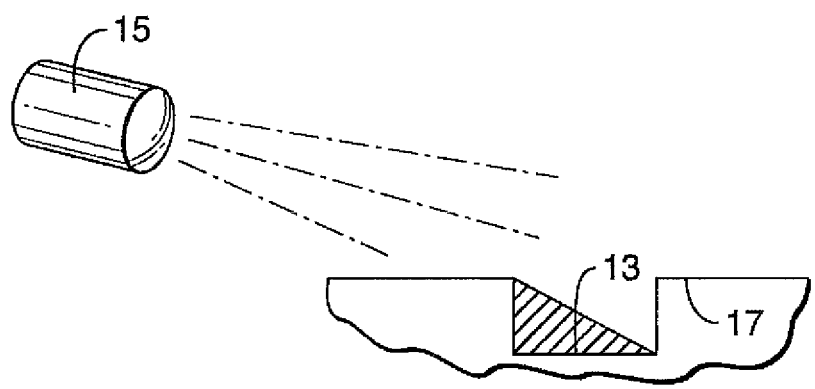

For example, referring to FIGS. 8A and 8B, the teachings of the present disclosure are illustrated. As shown, in FIG. 8A, a base sheet 17 includes an embossment 11 formed into the base sheet. Similarly, in FIG. 8B, an embossment 13 is formed into the base sheet 17. The embossment 13 has a depth greater than the embossment 11. When a light source 15 emits light onto the base sheet 17 at an angle, a shadow is formed in the embossments 11 and 13. As shown, the shadow in the embossment 13 is wider than the shadow that is created in embossment 11. The shadow that is created in the embossments 11 and 13 is visible. Thus, the deeper embossment 13 would appear to have a heavier line weight than the embossment 11 even though the embossment 13 has the same width or may even be shorter in width than the embossment 11.

Figure 2:
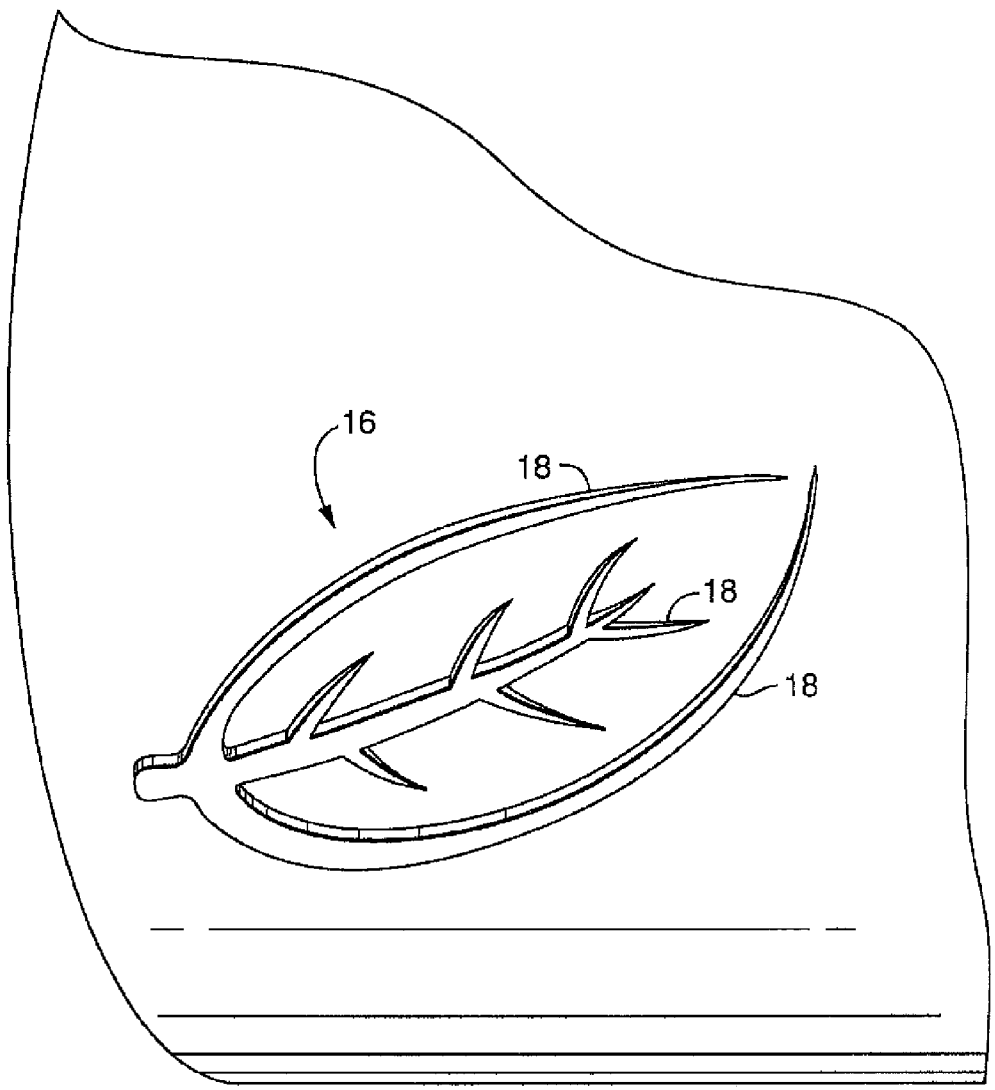
FIG. 2 is a perspective view of one embodiment of an embossing element in accordance with the present disclosure.

Referring to FIG. 2, an embossing pattern made in accordance with the present disclosure is illustrated. As shown, in FIG. 2, an embossing element 16 in the shape of a leaf similar to the embossing element shown in FIG. 1 is illustrated. As shown, the embossing element 16 includes a plurality of raised line portions 18. The line portions 18 gradually decrease in width. In accordance with the present disclosure, in addition to gradually decreasing in width, the line elements also gradually decrease in depth. The decrease in depth allows for the graduated line weights to be visible when the embossing element 16 is embossed into a sheet material as illustrated in FIGS. 8A and 8B.

Figure 3:
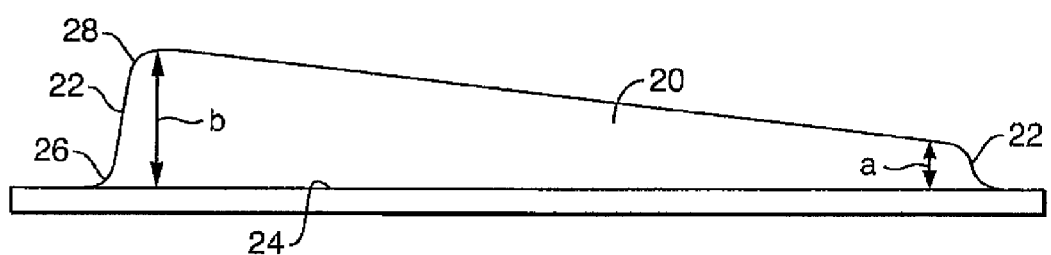
FIG. 3 is a side view of another embodiment of an embossing element made in accordance with the present disclosure.

Referring to FIG. 3, for purposes of illustration, a raised portion 20 that may be part of an embossing pattern in accordance with the present disclosure is shown. The raised portion 20, for example, is intended to be used to emboss a sheet material. The raised portion 20 can be part of a larger design that is intended to improve the aesthetic appeal of an embossed product.

As shown, the raised portion 20 has a gradually decreasing profile which, when used to emboss a sheet material, forms a line element in the sheet material that has a gradually decreasing depth. As shown, the raised portion 20 includes a maximum height (b) that gradually decreases to a minimum height (a).

The height of the raised portion 20 can vary dramatically depending upon various factors including the type of material being embossed and the desired effect. For exemplary purposes only, in one embodiment, the minimum height (a) of the raised portion 20 is at least about 0.005 inches. The maximum height (b) of the raised portion 20 can be at least about 0.005 inches greater than the minimum height (a). In one particular embodiment, for instance, the minimum height (a) and the maximum height (b) can both fall within a range of from about 0.005 inches to about 0.2 inches. For instance, the minimum height can be from about 0.005 inches to about 0.1 inches, while the maximum depth can be from about 0.005 inches to about 0.06 inches greater than the minimum depth. In one embodiment, the minimum height (a) can be about 0.02 inches, while the maximum height (b) can be about 0.06 inches. In an alternative embodiment, the minimum height (a) may be about 0.02 inches, while the maximum height (b) can be about 0.04 inches.

The maximum height (b), also known as the engraving depth, of the raised portion 20 can vary as described above depending, for instance, on the embossing pattern and the application. Greater heights are typically used for applications which require a very large increase in bulk. Lower heights, on the other hand, are used in situations which require a very dense finished product with clearly visible embossing.

Embossing elements such as the raised portion 20 as shown in FIG. 3 generally include slanted side walls 22. The side walls 22, for instance, typically form an angle with a base 24 of from about 20° to about 30°, such as about 25°. Shallower side walls are typically easier to engrave and keep clean. Steeper side walls, on the other hand, are better for embossing clarity and ply attachment, particularly when using steel to steel embossing.

Embossing elements such as raised element 20 can also include a bottom radius of curvature 26 and a top radius of curvature 28. The radii can be the same or different and can range from about 0.001 inches to about 0.01 inches, such as about 0.005 inches. Larger radii may be easier to engrave and result in less degradation at a given embossing level while smaller radii can be better for embossing clarity and result in more bulk at a given embossing level.

In order for the raised element 20 to form an embossment within a sheet material having a perceived line weight variation, the gradual decrease in height of the raised portion should occur over a length of at least about 0.15 inches, such as from about 0.5 inches to about 10 inches or greater. For example, the length of the raised portion 20, and therefore the length of the line element formed into the sheet material can be generally greater than about 1 inch, such as greater than about 2 inches, such as from about 1 inch to about 5 inches. In the embodiment illustrated in FIG. 3, the length of the raised portion 20 is linear. In other embodiments, however, the length of the raised portion 20 may include curved portions, such as the raised portions 18 shown in FIG. 2.

In the embodiment illustrated in FIG. 3, the height profile of the raised portion 20 gradually and continuously decreases from the maximum height (b) to the minimum height (a). In other embodiments, however, the gradual decrease in height can be accomplished in a stepwise manner. For instance, at the dimensions described above, the height of the raised portion can gradually decrease in steps that have a height differential of no more than about 0.005 inches.

Figure 6:
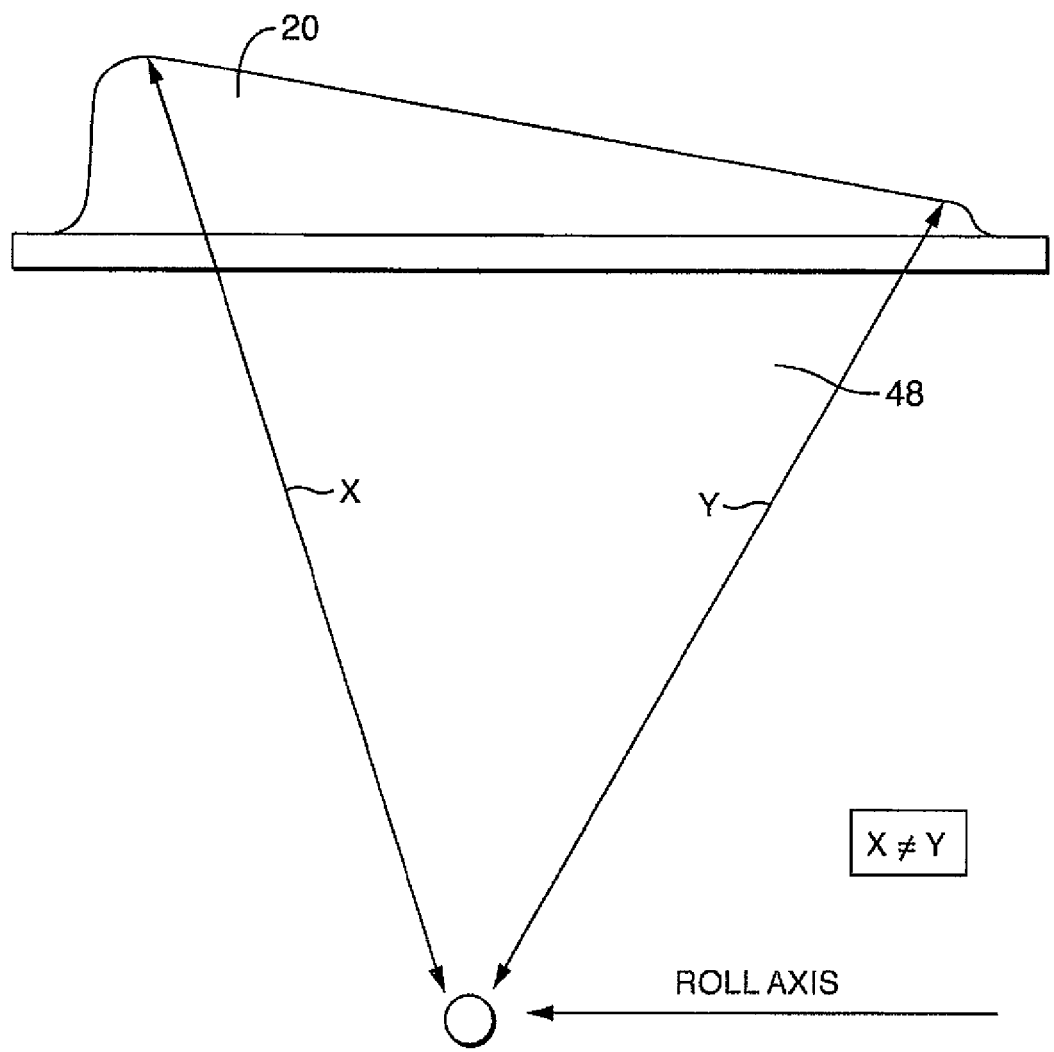
FIG. 6 is a partial cross-sectional view of one embodiment of an embossing roller in accordance with the present disclosure.
Figure 7:
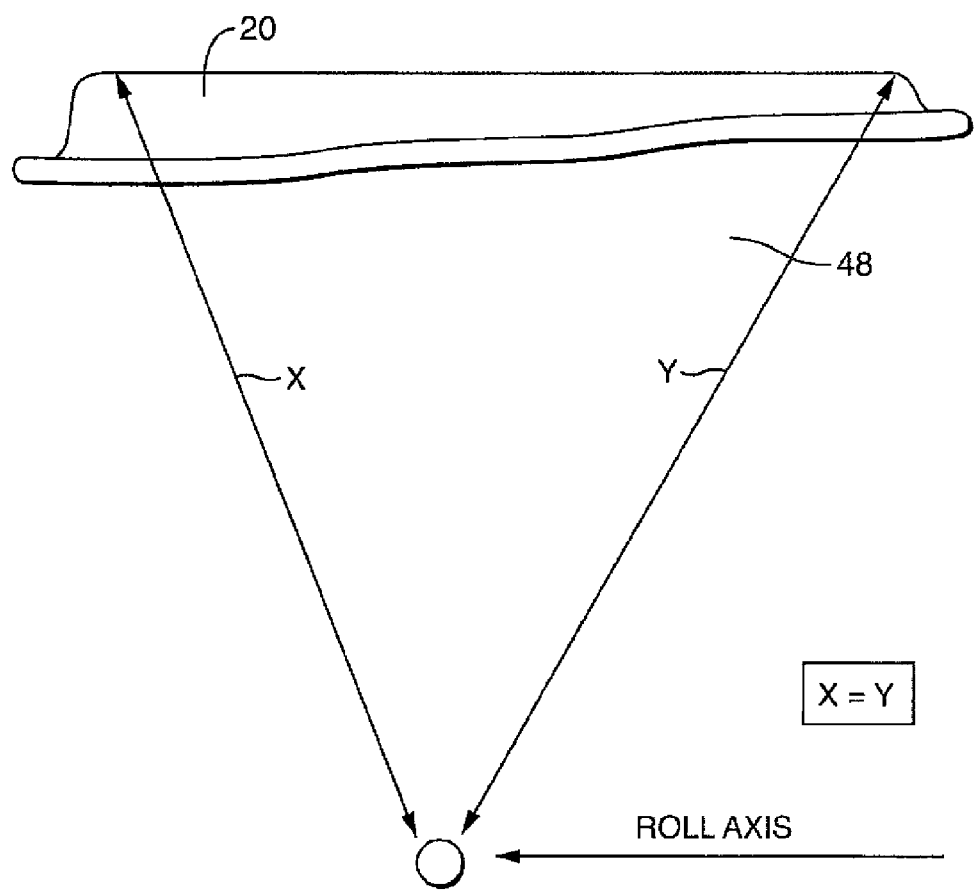
FIG. 7 is a partial cross-sectional view of another embodiment of an embossing roller in accordance with the present disclosure.

As described above, the raised portion 20 may, in one embodiment, be incorporated into an embossing roller that is used to emboss a sheet material. The embossing roller, for instance, can include a cylindrical surface from which the raised portion extends as shown in FIGS. 6 and 7. In one embodiment, the cylindrical surface can have a constant diameter as shown particularly in FIG. 6. In this embodiment, the distance between the top surface of the raised portion 20 and the axis of the embossing roller vary as the height of the raised portion varies.

In an alternative embodiment, the cylindrical surface of the embossing roll 48 can have a changing diameter as shown in FIG. 7. When the cylindrical surface has a changing diameter, for instance, the embossing roller 48 may be configured such that the top surface of the raised portion 20 is always the same distance from the roll axis even as the height of the raised portion changes. In this embodiment, for instance, the top surface of the raised portion 20 may have a constant diameter from the roll axis.

Figure 4:
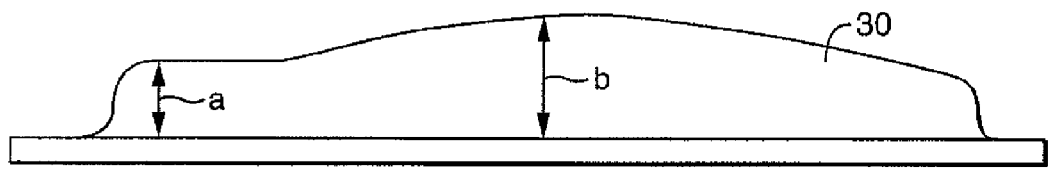
FIG. 4 is a side view of still another embodiment of an embossing element in accordance with the present disclosure.

In FIG. 3, the height profile of the raised portion 20 is somewhat simple in that it gradually decreases from a maximum height to a minimum height along the length of the structure. Referring to FIG. 4, an alternative embodiment of a raised portion 30 made in accordance with the present disclosure is shown that has a somewhat more complex height profile.

The raised portion 30 as shown in FIG. 4 includes a minimum height (a) and a maximum height (b). In this embodiment, however, the height of the raised portion 30 gradually increases from the minimum height (a) to the maximum height (b) and then gradually decreases back to the minimum height (a). Thus, when embossed into a sheet material, the raised portion 30 will create a line element in the sheet material that will appear to have an increasing line weight followed by a decreasing line weight.

In general, any suitable sheet material can be embossed in accordance with the present disclosure. For instance, in one embodiment, the sheet material being embossed can comprise a tissue product, such as a paper towel, an industrial wiper, a facial tissue, a bath tissue, a napkin, a premoistened wipe, and the like.

Tissue webs processed according to the present disclosure can be made in different manners and can contain various different types of fibers. In general, the tissue webs will contain pulp fibers in an amount of at least about 30% by weight and will have a bulk of at least 3 cc/g. In one embodiment, for instance, the tissue web can contain softwood fibers. In addition to softwood fibers, the tissue web can also contain hardwood fibers, such as eucalyptus fibers, and/or high-yield pulp fibers. As used herein, "high-yield pulp fibers" are those papermaking fibers produced by pulping processes providing a yield of about 65 percent or greater, more specifically about 75 percent or greater, and still more specifically from about 75 to about 95 percent. Yield is the resulting amount of processed fiber expressed as a percentage of the initial wood mass. Such pulping processes include bleached chemithermomechanical pulp (BCTMP), chemithermomechanical pulp (CTMP) pressure/pressure thermomechanical pulp (PTMP), thermomechanical pulp (TMP), thermomechanical chemical pulp (TMCP), high-yield sulfite pulps, and high-yield kraft pulps, all of which leave the resulting fibers with high levels of lignin. High-yield fibers are well known for their stiffness (in both dry and wet states) relative to typical chemically pulped fibers. The cell wall of kraft and other non-high-yield fibers tends to be more flexible because lignin, the "mortar" or "glue" on and in part of the cell wall, has been largely removed. Lignin is also nonswelling in water and hydrophobic, and resists the softening effect of water on the fiber, maintaining the stiffness of the cell wall in wetted high-yield fibers relative to kraft fibers. The preferred high-yield pulp fibers can also be characterized by being comprised of comparatively whole, relatively undamaged fibers, high freeness (250 Canadian Standard Freeness (CSF) or greater, more specifically 350 CFS or greater, and still more specifically 400 CFS or greater), and low fines content (less than 25 percent, more specifically less than 20 percent, still more specifically less that 15 percent, and still more specifically less than 10 percent by the Britt jar test).

In one embodiment of the present invention, the tissue web contains softwood fibers in combination with high-yield pulp fibers, particularly BCTMP fibers. BCTMP fibers can be added to the web in order to increase the bulk and caliper of the web, while also reducing the cost of the web.

The amount of high-yield pulp fibers present in the sheet can vary depending upon the particular application. For instance, the high-yield pulp fibers can be present in an amount of about 2 dry weight percent or greater, particularly about 15 dry weight percent or greater, and more particularly from about 5 dry weight percent to about 40 dry weight percent, based upon the total weight of fibers present within the web.

In one embodiment, the tissue web can be formed from multiple layers of a fiber furnish. The tissue web can be produced, for instance, from a stratified headbox. Layered structures produced by any means known in the art are within the scope of the present invention, including those disclosed in U.S. Pat. No. 5,494,554 to Edwards, et al. and U.S. Pat. No. 5,129,988 to Farrington, which are incorporated herein by reference.

Stratified base webs can be formed using equipment known in the art, such as a multilayered headbox. Both strength and softness of the base web can be adjusted as desired through layered tissues, such as those produced from stratified headboxes.

For instance, different fiber furnishes can be used in each layer in order to create a layer with the desired characteristics. For example, layers containing softwood fibers have higher tensile strengths than layers containing hardwood fibers. Hardwood fibers, on the other hand, can increase the softness of the web. In one embodiment, a base web can be produced that includes a first outer layer and a second outer layer containing primarily hardwood fibers. The hardwood fibers can be mixed, if desired, with paper broke in an amount up to about 10% by weight and/or softwood fibers in an amount up to about 10% by weight. The base web can further include a middle layer positioned in between the first outer layer and the second outer layer. The middle layer can contain primarily softwood fibers. If desired, other fibers, such as high-yield fibers or synthetic fibers may be mixed with the softwood fibers.

When constructing a web from a stratified fiber furnish, the relative weight of each layer can vary depending upon the particular application. For example, in one embodiment, when constructing a web containing three layers, each layer can be from about 15% to about 40% of the total weight of the web, such as from about 25% to about 35% of the weight of the web.

In still another embodiment, a base web can be made containing two layers of fibers. The first layer can contain high-yield pulp fibers. The second layer, on the other hand, can comprise softwood fibers. This particular embodiment is well suited for creating two-ply products. In particular, the layers of fibers containing the high-yield fibers can be laminated to a second nonwoven web in forming the multi-ply product.

The tissue web of the present invention can also be formed without a substantial amount of inner layer fiber-to-fiber bond strength. In this regard, the fiber furnish used to form the base web can be treated with a chemical debonding agent. The debonding agent can be added to the fiber slurry during the pulping process or can be added directly into the head box. Suitable debonding agents that may be used in the present invention include cationic debonding agents such as fatty dialkyl quaternary amine salts, mono fatty alkyl tertiary amine salts, primary amine salts, imidazoline quaternary salts, silicone quaternary salt and unsaturated fatty alkyl amine salts. Other suitable debonding agents are disclosed in U.S. Pat. No. 5,529,665 to Kaun which is incorporated herein by reference. In particular, Kaun discloses the use of cationic silicone compositions as debonding agents.

In one embodiment, the debonding agent used in the process of the present invention is an organic quaternary ammonium chloride and particularly a silicone based amine salt of a quaternary ammonium chloride. For example, the debonding agent can be PROSOFT TQ1003 marketed by the Hercules Corporation. The debonding agent can be added to the fiber slurry in an amount of from about 1 kg per metric tonne to about 10 kg per metric tonne of fibers present within the slurry.

In an alternative embodiment, the debonding agent can be an imidazoline-based agent. The imidazoline-based debonding agent can be obtained, for instance, from the Witco Corp. of Middlebury, Conn. The imidazoline-based debonding agent can be added in an amount of between 2.0 to about 15 kg per metric tonne.

In one embodiment, the debonding agent can be added to the fiber furnish according to a process as disclosed in PCT Application having an International Publication No. WO 99/34057 filed on Dec. 17, 1998 or in PCT Published Application having an International Publication No. WO 00/66835 filed on Apr. 28, 2000, which are both incorporated herein by reference. In the above publications, a process is disclosed in which a chemical additive, such as a debonding agent, is adsorbed onto cellulosic papermaking fibers at high levels. The process includes the steps of treating a fiber slurry with an excess of the chemical additive, allowing sufficient residence time for adsorption to occur, filtering the slurry to remove unadsorbed chemical additives, and redispersing the filtered pulp with fresh water prior to forming a nonwoven web.

The manner in which the tissue web is formed can vary depending upon the particular application. In general, the tissue web can be formed by any of a variety of papermaking processes known in the art. For example, the tissue web can be formed from an aqueous suspension of fibers or can be air formed. When formed from an aqueous suspension of fibers, the tissue web can be a wet-creped web, a calendered web, a through-air dried web, a creped through-air dried web, an uncreped through-air dried web, as well as various combinations of the above.

The basis weights of tissue webs can also vary depending upon the final product. In general, the basis weight of tissue webs can vary from about 10 gsm to about 120 gsm, such as from about 20 gsm to about 80 gsm.

As stated above, tissue webs generally have a bulk of greater than about 3 cc/g. For example, the tissue web can have a bulk of greater than about 8 cc/g, such as greater than about 9 cc/g, such as even greater than about 10 cc/g. For instance, the bulk can vary from about 8 cc/g to about 12 cc/g or greater.

The base sheet embossed in accordance with the present disclosure can be a single ply sheet or can be a multi-ply sheet. For instance, in one embodiment, one or more tissue webs can be combined together in forming the product. Each tissue web can be made according to the same process or a different process. The plies can be embossed according to the present disclosure prior to being combined together, while the plies are being combined together, or after the plies have been combined together. In one particular embodiment, the embossing process can be used to attach two or more plies together.

When forming a multi-ply product, the different plies can be held together through crimping, through pressure bonds, by using an adhesive, or using any other suitable technique. When using an adhesive or binder, any suitable adhesive may be used. For instance, the adhesive can be applied to one or both webs to join the webs together. The adhesive can be, for instance, a latex adhesive, a starch-based adhesive, an acetate such as ethylene vinyl acetate adhesive, a polyvinyl alcohol adhesive, and the like.

In one embodiment, one or both plies can be sprayed with an adhesive as the plies are embossed together. In an alternative embodiment, at least one of the plies can be embossed and an adhesive can be applied to the embossed portions that protrude from the surface of the ply for attachment to an opposite ply. For example, in one embodiment, an offset printer can be used in which a first roller is dipped into an adhesive. The adhesive is transferred to a second roller and then to a third roller before being applied to one of the plies. In one embodiment, the third roller can be configured to contact the tissue web where the tissue web protrudes due to the embossments. Once the adhesive is applied, the ply can then be adhered to an opposing ply.

The embossing process of the present disclosure is generally performed on tissue webs after the webs have been formed and dried. For example, in one embodiment, after the tissue web has been formed and dried, the tissue product may undergo a converting process and subjected to an embossing process in accordance with the present disclosure.

Figure 5:
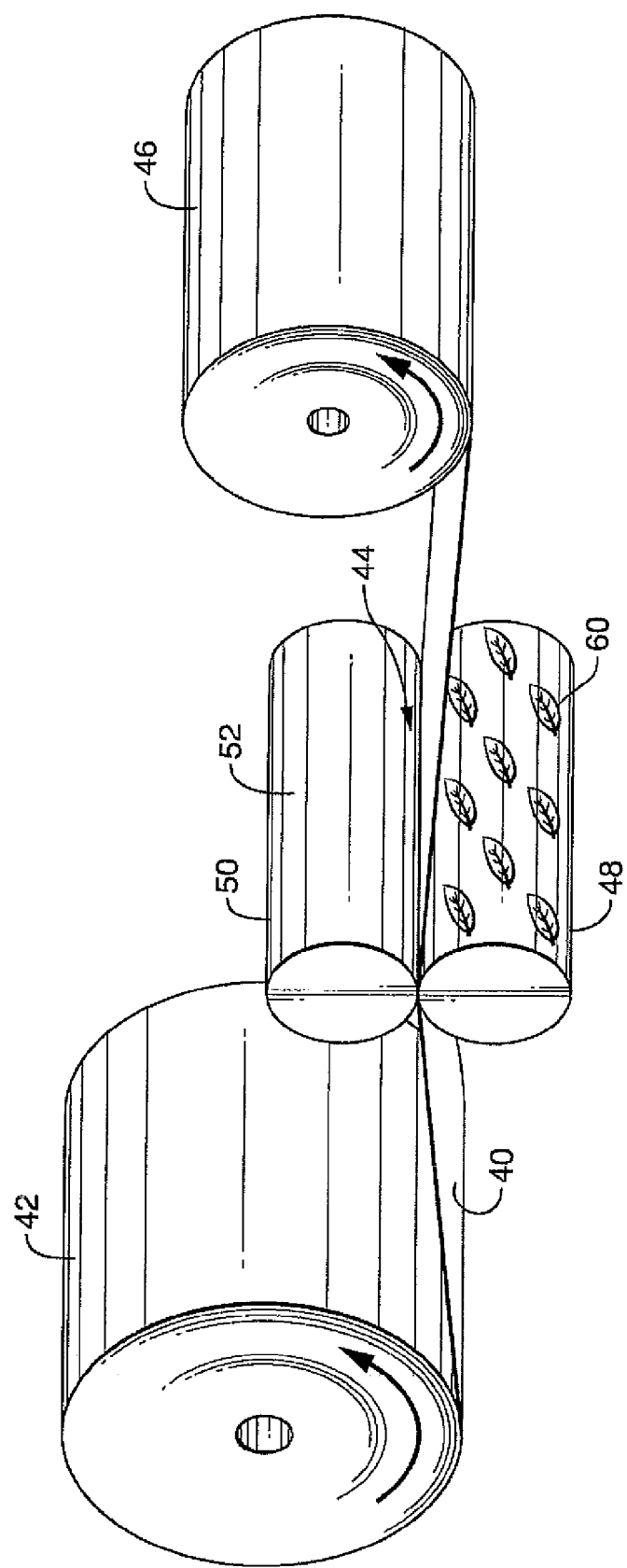
FIG. 5 is a perspective view of one embodiment of an embossing process in accordance with the present disclosure.

For exemplary purposes only, referring to FIG. 5, one embodiment of a process for embossing a sheet material in accordance with the present disclosure is shown. As illustrated, a sheet material 40 is unwound from a supply roll 42 and fed through a nip 44 where the sheet material is embossed. After exiting the nip 44, the sheet material 40 is then rewound into a roll 46.

The nip 44 is formed between a pattern or embossing roller 48 and a backing roller 50. The embossing roller 48 includes an embossing pattern in accordance with the present disclosure and can be made from any suitable hard material, such as steel. As shown, the embossing roller 48 includes a plurality of raised portions 60 that include at least one line portion having a gradually decreasing height. As described above, when formed into the sheet material 40, the gradually decreasing height produces an embossment having a perceived reducing line weight.

The backing roller 50 can have a hard surface or a compressible surface. For example, the backing roller 50 can include a steel surface or, alternatively, can include a rubber or elastomeric coating 52 as shown in FIG. 5. As described above, sheet materials embossed in accordance with the present disclosure are generally embossed when substantially dry. For example, for many applications, the sheet material can have a moisture content of less than about 6%.

In addition to the above described tissue products, it should be understood that any suitable nonwoven material may be embossed in accordance with the present disclosure. Other nonwoven materials that may be produced include meltspun webs such as meltblown webs and spunbond webs, bonded carded webs, hydroentangled webs, and laminates thereof, such as spunbond/meltblown/spunbond webs.

When embossing a nonwoven web containing primarily synthetic fibers, for instance, the embossing process may be carried out with the presence of heat and/or ultrasonic energy in order to assist in forming the embossments. In this embodiment, the embossing process may also form bonds between multiple layers of material.

As used herein, a "meltblown web" refers to a web made from fibers formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin. et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbond web" refers to a web made from small diameter substantially continuous fibers that are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers can sometimes have diameters less than about 40 microns, and are often between about 5 to about 20 microns.

As described above, the sheet material may also contain a hydroentangled nonwoven fabric. Hydroentangling processes and hydroentangled composite webs containing various combinations of different fibers are known in the art. A typical hydroentangling process utilizes high pressure jet streams of water to entangle fibers and/or filaments to form a highly entangled consolidated fibrous structure, e.g., a nonwoven fabric. Hydroentangled nonwoven fabrics of staple length fibers and continuous filaments are disclosed, for example, in U.S. Pat. No. 3,494,821 to Evans and U.S. Pat. No. 4,144,370 to Bouolton, which are incorporated herein in their entirety by reference thereto for all purposes. Hydroentangled composite nonwoven fabrics of a continuous filament nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes.

The sheet material may also contain a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

In one embodiment, after the sheet material has been embossed, the sheet material may be used to form a premoistened wipe. In this embodiment, the embossed sheet material is saturated with a wiping solution. The wiping solution may comprise, for instance, a water and alcohol solution. Alternatively, the wiping solution may comprise water in combination with various surfactants.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An embossed product comprising:
   a base sheet containing natural fibers, synthetic fibers or mixtures thereof, the base sheet having a first side and a second and opposite side;
   a pattern embossed into the first side of the base sheet, the embossed pattern including a decorative feature that includes at least one line element wherein the depth of the embossed pattern along the line element only decreases in a continuous manner from a first end of the line element where the line element originates to a second and opposite end of the line element where the line element terminates making the line element appear to have a decreasing line weight;
   the line element having a minimum depth of at least 0.005 inches at the first end of the line element and a maximum depth at the second and opposite end of the line element;
   wherein the line element has a width and wherein the width of the line element also decreases as the depth of the embossed pattern gradually decreases;
   wherein the decorative feature is formed from a plurality of line elements integrally cooperating to form an image in the embossed product; and
   wherein the base sheet has a bulk of at least 3 cc/g.

2. An embossed product as defined in claim 1, wherein the line element has a length of at least 0.15 inches.

3. An embossed product as defined in claim 1, wherein the depth of the embossed pattern along the line element decreases from a maximum depth to a minimum depth, the minimum depth being at least 0.005 inches, the difference between the maximum depth and the minimum depth being at least 0.005 inches.

4. An embossed product as defined in claim 1, wherein the line element is part of a decorative feature embossed into the base sheet.

5. An embossed product as defined in claim 1, wherein the base sheet contains pulp fibers in an amount greater than 50% by weight and has a bulk of at least 3 cc/g.

6. An embossed product as defined in claim 1, wherein the base sheet comprises at least two plies.

7. An embossed product as defined in claim 3, wherein the depth of the embossed pattern along the line element is in between about 0.02 inches to about 0.15 inches.

8. The embossed product of claim 1, wherein the plurality of line elements forming the decorative feature include both linear and curved line elements integrally cooperating.

9. An embossed product comprising:
   a base sheet containing natural fibers, synthetic fibers or mixtures thereof, the base sheet having a first side and a second and opposite side;
   a pattern embossed into the first side of the base sheet, the embossed pattern including at least one line element wherein the depth of the embossed pattern along the line element only decreases making the line element appear to have a decreasing line weight;
   wherein the depth of the embossed pattern along the line element decreases gradually in a continuous manner from a first end of the line where the line element originates element to a second and opposite end and there is a minimum depth at the first end of the line element and a maximum depth at the second and opposite end of the line element where the line element terminates;
   wherein the line element has a width and wherein the width of the line element decreases as the depth of the embossed pattern gradually decreases; and
   wherein the pattern is formed from a plurality of line elements integrally cooperating to form an image in the base sheet.

10. The embossed product of claim 9, wherein the plurality of line elements forming the pattern include both linear and curved line elements integrally cooperating.

11. A process for embossing a sheet-like product comprising:
    feeding a base sheet into a nip formed between an embossing roller and a backing roller, the embossing roller including raised portions that emboss a pattern into the base sheet, the raised portions including at least one line portion that has a gradually decreasing profile that embosses a corresponding line element into the base sheet, the line element having only a decreasing depth that decreases in a continuous manner from a first end of the line element where the line element originates to a second and opposite end of the line element where the line element terminates and there is a minimum depth at the first end of the line element and a maximum depth at the second and opposite end of the line element, making the line element appear to have a decreasing line weight wherein the base sheet has a bulk of at least 3 cc/g wherein the depth of the embossed pattern along the line element decreases gradually from a first end of the line element to a second and opposite end;
    wherein the line portion has a width and wherein the width of the line portion also decreases as the profile of the line portion decreases; and
    wherein the pattern is formed from a plurality of line portions integrally cooperating to form an image in the base sheet.

12. A process as defined in claim 11, wherein the backing roller includes an exterior surface made from a compressible material.

13. A process as defined in claim 11, wherein the at least one line portion has a length of at least 0.15 inches.

14. A process as defined in claim 11, wherein the line element embossed into the base sheet has a minimum depth and a maximum depth, the minimum depth being at least 0.005 inches, the difference between the maximum depth and the minimum depth being at least 0.005 inches.

15. A process as defined in claim 11, wherein the base sheet contains pulp fibers in an amount of at least 50% by weight and has a bulk of at least 3 cc/g.

16. A process as defined in claim 11, wherein the base sheet includes at least two plies, at least one of the plies containing pulp fibers.

17. A process as defined in claim 11, wherein the line element embossed into the base sheet has a minimum depth and a maximum depth, the minimum depth and the maximum depth falling within a range of from about 0.02 inches to about 0.15 inches.

18. A process as defined in claim 11, wherein the embossing roller includes a base cylindrical portion from which the raised portions extend, the base cylindrical portion having a constant diameter.

19. A process as defined in claim 11, wherein each of the raised portions on the embossing roller have a top surface and wherein the embossing roller defines a roll axis and wherein the top surface of every raised portion is equal distance from the roll axis.

* * * * *